United States Patent [19]

Myatt

[11] 4,260,555

[45] Apr. 7, 1981

[54] PROCESS FOR THE MANUFACTURE OF CYANOOXIMINONITRILES

[75] Inventor: Hal L. Myatt, Greensboro, N.C.

[73] Assignee: Ciba-Geigy Corporation, Ardsley, N.Y.

[21] Appl. No.: 92,256

[22] Filed: Nov. 7, 1979

[51] Int. Cl.³ .......................................... C07C 120/00
[52] U.S. Cl. ................................ 260/465 E; 549/75; 260/347.7; 260/465 R; 71/105
[58] Field of Search .......... 549/75; 260/465 E, 347.7; 71/105

[56] References Cited

U.S. PATENT DOCUMENTS

| | | | |
|---|---|---|---|
| 4,070,389 | 1/1978 | Martin | 260/465 E |
| 4,081,551 | 3/1978 | Welfe et al. | 260/465 E |
| 4,123,255 | 10/1978 | Freenor et al. | 71/103 |
| 4,158,015 | 6/1979 | Paul | 549/75 X |

FOREIGN PATENT DOCUMENTS

68/2699  4/1968  South Africa .

*Primary Examiner*—Joseph P. Brust
*Attorney, Agent, or Firm*—Karl F. Jorda

[57] ABSTRACT

A process for the manufacture of O-cyano(substituted-)alkyloximinoaryl nitriles of the formula:

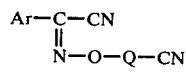

wherein Ar is substituted or unsubstituted aryl or heterocyclic moiety and Q is a lower alkyl or phenalkyl moiety, is described. The process comprises the condensation of a cyanosulfonate of the formula:

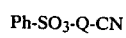

wherein $Ph-SO_3-$ is an aromatic protecting group with Ph being unsubstituted or p-methyl-substituted phenyl, with an oximinoaryl nitrile of the formula:

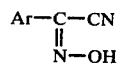

The condensation reaction is preferably initiated in immiscible solvents for each reactant and in the presence of a phase-transfer catalyst. Also included are the steps of preparing the oximinoaryl nitrile and an isomerization step whereby any trans-isomer that is found is converted to the desirable cis-isomer.

12 Claims, No Drawings

PROCESS FOR THE MANUFACTURE OF CYANOOXIMINONITRILES

FIELD OF THE INVENTION

The present invention relates to the production of oxime ethers useful for the promotion of plant growth and as species-specific antidotes against general herbicides, and more particularly to the production of O-cyano(substituted)alkyloximinoaryl nitriles.

BACKGROUND OF THE INVENTION

In the preparation of soil for the cultivation of millet and rice, it is a common expedient to use potent general herbicides such the chloroacetanilides and thiocarbamates. While such herbicides effectively kill the undesired vegetation (weeds), residues thereof interfere with the cultivation of the desirable crops by inhibiting their growth. It has been found that phenylglyoxylonitrile-2-oxime-cyanomethyl ether and related compounds, as described in U.S. Pat. No. 4,070,389, issued Jan. 24, 1978, and co-pending U.S. Pat. Applications, Ser. Nos. 881,953 and 939,096, filed Feb. 27, 1978 and Sept. 1, 1978, respectively, both now abandoned, act as species-specific antidotes or "safeners". Use of such safeners permits the cultivation of desired cereal and other crops even in the presence of previously toxic amounts of herbicides.

As set forth in the aforementioned U.S. Pat. No. 4,070,389, and in co-pending U.S. patent applications Ser. Nos. 881,953 and 939,096, the compounds are produced by the etherification of an oxime or oxime salt of formula I

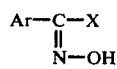

(I)

with a halide of the formula

Hal-Q wherein Ar, X, Hal and Q have the meanings described therein.

Previously, the syntheses of the oximes or oxime salts of the above required the use of sodium methoxide as an intermediate in the reaction of the nitrite ester and the aryl acetonitrile. Sodium methoxide is an expensive and hazardous material.

Furthermore, the preparation of these oximes or oxime salts also involved the use of halides (Hal-Q compounds) which are very costly and toxic.

DETAILED DISCLOSURE OF THE INVENTION

It is an object of this invention to provide a simple process for the manufacture of compounds of the formula:

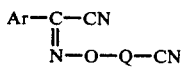

(I)

wherein Q represents lower alkylene or phenalkylene

Ar represents substituted or unsubstituted aryl or a heterocyclic group, such as, a phenyl group of the formula:

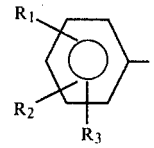

and α- or β-naphthyl group, or a heterocyclic group of the formula:

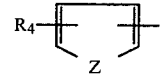

$R_1$ represents hydrogen, halogen, lower alkyl, lower alkoxy, or a phenoxy group which is in the para-position and which is optionally substituted a maximum of twice by halogen, CN, $NO_2$ or $CF_3$;

$R_2$ and $R_3$, independently, represent hydrogen, halogen, $NO_2$, lower alkyl, lower halogenoalkyl, or lower alkoxy;

$R_4$ represents hydrogen, halogen, lower alkyl, lower alkoxy, $NO_2$; and

Z represents oxygen or sulfur.

Halogen, mentioned above, includes fluorine, chlorine, bromine, or iodine; lower alkyl alone or as part of a moiety means straight or branched $C_1$-$C_4$ alkyl groups.

The process of this invention includes the following steps:

A(1) 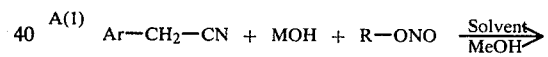

(II) (III)

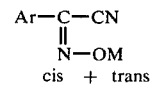

(IV)

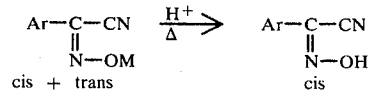

A(2)

(IV) (V)

B Ph—$SO_2$X + MCN + O=Q $\xrightarrow[\text{Solvent}]{\text{Cat.}}$ (VI)

Ph—$SO_3$—Q—CN + MX (VII)

C Ph—$SO_3$—Q—CN + 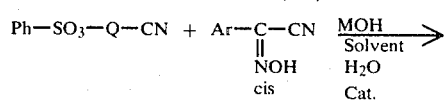 $\xrightarrow[\substack{\text{Solvent} \\ H_2O \\ \text{Cat.}}]{\text{MOH}}$ (VII) (V)

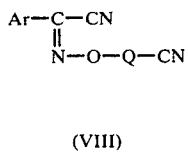

(VIII)

wherein Ar and Q have the meanings given above,
R is lower alkyl of 1–5 C atoms
Ph is phenyl or p-methyl-substituted phenyl,
X is halogen, preferably chlorine
M is an alkali metal.

Step A (1) describes the preparation of an oximinoaryl nitrile (IV) by the reaction of an alkyl nitrile ester (III) with aryl acetonitrile (II) in the presence of an alkali metal hydroxide or such as, preferably sodium hydroxide or potassium hydroxide.

The prior art teaches that sodium methoxide is needed as the base source for the reaction of the nitrile ester (III) and the nitrile (II). This reagent is expensive and difficult to handle. It was previously believed that only such a strong base source as the alkali methoxide would promote the reaction. The present invention substitutes an alkali metal hydroxide for this expensive and hazardous material.

Any alkyl nitrite ester (III) is operative in the process. Isopropyl nitrite is preferable because of the convenient boiling point of the by-product isopropanol and the fact that isopropanol does not form an azeotrope with the preferred solvent, i.e. xylene, thus expediting the recovery of the solvent and the by-product.

The prior art teaches that in this type of a reaction a mixture of cis-trans isomers is formed and describes a laborious method for isomer separation including isolation of the sodium salt of the product, followed by an extraction series with isopropanol to separate the trans-isomer from the cis-isomer. The cis-isomer is preferred although both are biologically active.

The trans-isomer was then, according to the prior art, isolated and either discarded, photochemically isomerized or neutralized and thermally isomerized in refluxing solvents. At best, the yield of the preferred cis-isomer was about 75%.

The present invention increases the direct yield of the desired cis-isomer without recourse to the prior art separation techniques.

In addition, by the method of this invention the need for handling of the sodium salt of the oximinophenyl acetonitrile as a powder, which if inhaled is a potentially toxic material, is eliminated.

The procedure of this invention also permits the selective isomerization of the small amounts of the undesired isomer to the desired isomer to procede in solution followed by the isolation, in good yield, of the desired isomer.

In the procedure for the reaction according to step A(1), the alkyl nitrile ester of formula (III), preferably isopropyl nitrite, is added to a mixture of the nitrile of formula (II), alkali metal hydroxide and a solvent mixture containing methanol. The only requirement for the reaction solvent medium is that it be inert to the reactants. The reaction is initiated, proceeds and is substantially completed in about 1 to 6 hours at a temperature in the range 10°–50° C. As the reaction is exothermic, slow addition of the nitrite ester and cooling is needed.

In step A(2) the reaction mixture is cooled, diluted with water and neutralized. The aqueous phase is removed. The organic phase is then heated to remove the alcohol by-product by distillation. The mixture is held at about 100°–110° C. for 1–3 hours to effect a thermal isomerization in solution to the desired isomer. Conversion is about 95% complete. The dissolved product in the organic phase has the formula (V).

Alternatively, the organic phase is removed prior to neutralization. The aqueous phase is neutralized, then heated to about 100° C. to effect the thermal isomerization.

Step B is directed to an improved method for the preparation of the cyanoalkyl arylsulfonates, such as, p-toluenesulfonate, benzenesulfonate, etc., that are used as intermediates in the synthesis scheme. This improved method for the preparation of these intermediates involved, in the case of p-toluenesulfonate, the reaction of p-toluenesulfonyl chloride with alkali metal cyanide and the appropriate aldehyde, ketone or benzophenone at a temperature ranging from about 0° to 20° C. In contrast to the known methods for preparing these sulfonates which require extended reaction times and large excesses of reagents and which have been characterized by poor yields, the present invention overcomes these shortcomings by the use of a novel catalyst.

This catalyst is a phase-transfer catalyst, typically a quaternary ammonium salt, and its use allows the reaction time to be reduced to as little as one hour. In addition, only a small excess of reagents need be used and improved yields result. In the preparation of cyanomethyl-p-toluenesulfonate from e.g. p-toluenesulfonyl chloride, formaldehyde, sodium cyanide, the reaction time is reduced to less than two hours. Yields of the literature reactions (without catalyst) are reported in the range 40–63%. By the use of the quaternary ammonium phase-transfer catalyst in 1–5 mole % amounts, the yields are increased to the 93–97% range.

As solvents for this catalytic reaction step any water-immiscible solvents may be used that are inert to the reactants. Aliphatic or aromatic hydrocarbons, as well as their chlorinated forms, such as, hexane, heptane, toluene, xylene, methylene chloride, ethylene dichloride, chlorobenzene, dichlorobenzene, etc. are satisfactory.

The catalysts, similarly, are not limited beyond their being quaternary ammonium, phosphonium, sulphonium, arsonium salts and have the ability to catalyze the reaction without permanently reacting with the reactants. Examples include tetramethylammonium chloride, tributylmethylammonium chloride, tetrabutylammonium bromide, cetyltrimethylammonium bromide, benzyltrimethylammonium bromide, tricaprylylmethylammonium chloride, octyltrimethylammonium chloride, dodecyltrimethylammonium chloride, benzyltriethylammonium chloride, dibenzyldiethylammonium nitrate, diethyldipropylammonium sulfate, dihexyldimethylammonium iodide, tetrabutylammonium hydrogen sulfate, tetrabutylphosphonium bromide, tetraethylphosphonium chloride, dioctadecenyldimethylammonium chloride, ethyltribenzyl phosphonium fluoride, cetyltrimethylphosphonium acetate, tricaprylylethylphosphonium nitrate, tributylhexadecylphosphonium bromide, tributylsulphonium bromide, tetrabutylphosphonium bromide and diethyldibenzylarsonium nitrate. Particularly preferred are benzyltrimethylammonium chloride, benzyltriethylammonium chloride, tributylmethylammonium chloride, tricaprylylmethylammonium chloride and tetrabutylammonium bromide.

The choice of the carbonyl reactant is governed by the nature of the Q group to be added to the oxime. Among such reactants may be aldehydes, such as, formaldehyde, acetaldehyde, benzaldehyde; ketones, such as, acetone, methyl ethyl ketone; and benzophenones, such as, benzophenone.

The replacement of sodium cyanide by other alkali metal cyanides is of course a permissible expedient. Similarly, vigorously reactive nitriles, such as, glycolonitrile in the presence of NaOH may serve as sources for the cyano group.

In the preparation of cyanoalkyl sulfonates, p-toluenesulfonyl chloride and especially benzenesulfonyl chloride are preferred as the initial reactants as they are inexpensive and are reagents with well recognized characteristics.

Step C is directed to that aspect of the invention wherein the oximinoaryl nitrile formed in the reaction shown in step A (1) and A (2) is reacted with the cyanoalkyl arylsulfonate formed in the reaction shown in step B.

Preferably, the step C reaction is carried out with both reaction components dissolved in suitable solvents for each. The oximino nitrile is dissolved in water in the presence of sufficient alkali metal hydroxide to form the alkali metal salt, preferably the sodium salt. The cyanoalkyl arylsulfonates, preferably, the p-toluene and benzene sulfonates, are dissolved in a water-immiscible solvent selected from those ennumerated above. The reaction takes place at the interface between the two liquids and is promoted by phase-transfer catalysts described above. The reaction is promoted by intimate contact between the immiscible aqueous and non-aqueous phases.

The reaction is best promoted with vigorous agitation of the two-phase solvent system at about 25°–140° C., in the presence of 1 to 5 mole % of catalyst, preferably about 2.5 mole %. Under such conditions, the reaction reaches equilibrum conditions within about two hours or less. The presence of catalyst is not requisite for the reaction to proceed but in the absence of catalyst the reaction time is extended considerably.

The product of the step C reaction is isolated by removing the aqueous phase and then removing the organic solvent in vacuo. Excellent yields of high purity product are obtained. The sulfonic acid by-products are removed with the aqueous phase as the alkali metal salt.

The multi-step process of this invention offers the following advantages over the direct and indirect teachings of the prior art procedures for the preparation of these compounds:

(a) The products are obtained in high yields and good purity and isomerization to the desired isomer is readily afforded.

(b) There is no loss in yield during the isomerization, as the procedure of this invention facilitates the "in situ" isomerization of the trans-isomer to the more desirable cis-isomer. Further this isomerization is simplified so that it may be carried out in the reaction vessel without specialized equipment.

(c) The intermediates are obtained in sufficient yield and purity at each stage so that they need no special purification after formation and thus can be utilized directly from solution. This eliminates any handling of the intermediates in the solid state. As some of the intermediates are hazardous, the handling of these in solution provides an additional measure of safety.

(d) The process uses less expensive intermediates which results in substantial savings.

PREFERRED EMBODIMENTS OF THE INVENTION

The preferred mode of carrying out this invention will be described and discussed with reference to the synthesis of phenylglyoxylonitrile-2-oxime-cyanomethyl ether as named in U.S. Pat. No. 4,070,389. This product is also called O-cyanomethyloximinophenylacetonitrile or O-cyanomethylphenyl glyoxylonitrile. The cis-isomer of this compound is commercialized as a sorghum "safener" for use where the land has been treated with herbicides of the chloroacetanilide or thiocarbamate classes. The use of the process of this invention for the preparation of other useful compounds to which it is applicable will be supplied in the additional examples.

The reaction chemistry and stoichiometry of the process of this invention is as set forth below for this compound.

A(1) C₆H₅CH₂CN + NaOH + 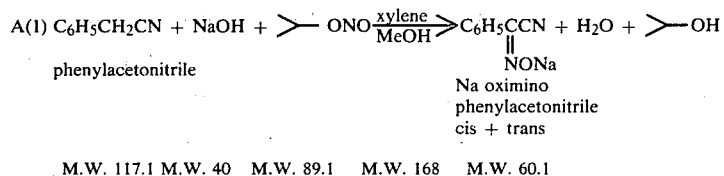

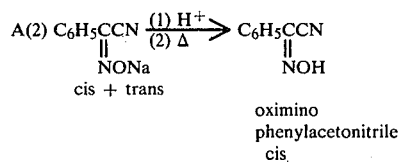

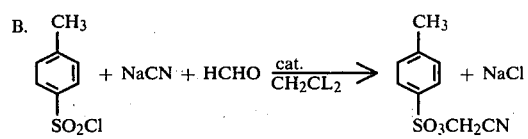

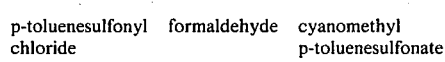

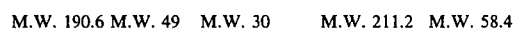

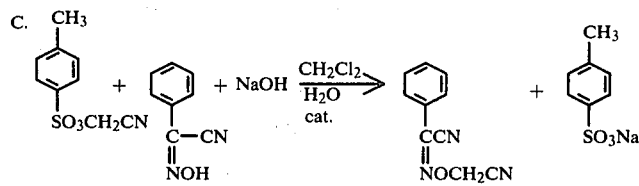

EXAMPLE 1

Step A. The Preparation of Oximinophenylacetonitrile

Into a three liter bottom-outlet reaction flask, fitted with mechanical stirrer, thermometer, reflux condenser, and dropping funnel is charged 900 g xylene, 96 g (3.0 mole) methanol, 175.6 g phenylacetonitrile (benzyl cyanide) (1.5 mole) and 100% excess 120 g (3.0 mole) sodium hydroxide pellets. The mixture is heated to 30°–40° C. and 140.1 g (1.58 mole) of isopropyl nitrite is added dropwise. Cooling is necessary to maintain the temperature range. Upon completion of the addition the reaction mixture is stirred for two hours at the stated temperature range. Greater than 99% conversion, based on phenylacetonitrile, is obtained. Then about 750 g water is added and the pH of the mix is adjusted to 3–5 with concentrated hydrochloric acid. The mixture is cooled to 20°–25° C., the layers are separated and the aqueous phase discarded. The organic phase is heated to 110° C. to distill the alcohols and to complete the thermal isomerization. The temperature is maintained at 100°–110° for one hour. The reaction mix is cooled and 800 g of water is added. The mix is adjusted to pH 12 with NaOH. When the temperature reaches 15°–20° C. the layers are split and the lower aqueous layer assayed for oximinophenylacetonitrile. The xylene is recycled.

Yield: A solution containing 20–25% of Na salt of oximinophenylacetonitrile, corresponding to a yield of 95–97% on phenylacetonitrile, is obtained. It comprises 94–96% cis-isomer.

Step B. The Preparation of Cyanomethyl p-Toluenesulfonate(CMTS)

Into a 3-liter reaction flask, equipped with condenser, mechanical stirrer, thermometer, and dropping funnel is charged 381.3 g p-toluenesulfonyl chloride (2.0 mole), and 1400 g methylene chloride. The resultant solution is cooled to 0° C. in an ice/salt bath, then 173 g of 37% formaldehyde (2.14 mole) and 18 g benzyltrimethylammonium chloride (Variquat B-200) (2 mole %) is added. A solution of 104.5 g sodium cyanide (2.14 mole) in 400 g of water is added while cooling at a rate such that the temperature remains 0°–10° C. The addition should be complete in less than 0.5 hour. The mixture is then stirred 1.5–2.5 hours at 0°–10° C. When p-toluenesulfonyl chloride conversion is complete, the layers are split, and the organic layer washed with water. The aqueous layer is treated with excess sodium hypochlorite to remove the residual cyanide and discarded.

Yield: A 22–23% solution is obtained, corresponding to a yield of 94–96%. On distillation of the solvent a light yellow to brown solid is obtained of greater than 98% purity.

Step C. The preparation of O-cyanomethylphenylacetonitrile

Into a 1-liter reaction flask equipped with a mechanical stirrer, reflux condenser, and dropping funnel is charged with 528.1 g of a 20% methylene chloride solution of cyanomethyl p-toluenesulfonate (CMTS) from Step B (0.50 mole), 12.0 g Variquat B-200, (5 mole %) and 20 g of water. The mixture is heated to reflux and 428.6 g of a 20% solution of the sodium salt of oximinophenylacetonitrile from Step A 1 (85.73 g, 0.51 mole) at pH 12 is added dropwise over a 10-15 minute period. The reaction is maintained at reflux for 2 hours. The pH is maintained above 10 by addition of NaOH if necessary. The layers are then split and the organic layer washed twice with 200 ml portions of water. The solvent is then removed on a rotary evaporator at 50° C. Last traces of solvent are removed by oil pump vacuum. Seeding may be necessary to induce crystallization of the dry product.

Yield: 90-92 grams of a reddish to light brown solid, corresponding to a yield of 97-99%. Yield is computed on CMTS and expressed in terms of total cis-, trans-isomer content. Typical material is 98-99% pure with a cis/trans ratio of 94:6.

EXAMPLE 2

Step A

A two-liter reactor is equipped with liquid seal agitator, addition funnel, thermometer, a reflux condenser with a Barrett water trap and a cooling bath or heating mantle. To the reactor is charged 365 g mixed xylenes, 81.9 g 98.2% caustic pellets (2.0 gmole), and 64.5 g methanol (2.0 gmole). The reactor is warmed to 40° C. and then 118.4 g 99.2% phenylacetonitrile (1.0 gmole) is charged to the reactor. To the addition funnel is charged 97.1 g 98.8% isopropyl nitrite (IPN; 1.07 gmole freshly prepared and kept cold until use). Addition of IPN to the reactor is started slowly at a rate to complete the charge in one hour. An ice bath is used to control the reaction temperature at 40° C. After the IPN charge, the reactor is held at 40° C. until gas chromatography shows total reaction of phenylacetonitrile (6'×¼" glass column, 3% O.V. 225). Then 300 g water is charged to dissolve the oximinophenylacetonitrile. Slowly about 212 g 37.4% HCL is charged to lower the pH to 4-5. Free oximinophenylacetonitrile dissolves in the xylene/alcohol phase. The lower water phase is removed and discarded. The xylene is heated to reflux (ca. 85° due to methanol) and the reflux temperature is adjusted to 100° C. by slowly removing alcohol distillates. The temperature is held at 100° C. for one hour then cooled to about 50° C. and 290 g water is charged. Next 50% caustic is slowly charged to raise the pH to 10.5 (stable). The lower aqueous layer is removed and weighed (~504 g typical) for titration analysis (32-33% typical). Yield is about 93% to 95%.

Step B

A 1500 ml, brine-jacketed, bottom outlet resin kettle is fitted with a liquid seal agitator, a thermometer, an addition funnel and a pH electrode and meter. A solution of 134.7 g 96% NaCN (2.64 gmole) and 300 g water is premixed and placed in the addition funnel. To the reactor 1000 g methylene chloride, 214.3 g 37% formaldehyde (15% methanol stabilized, 2.48 gmole) and 15.2 g 60% benzenetrimethylammonium chloride (BTMAC, 2 mole %) is charged. The reactor is cooled to <5° C. and 438 g as 100% benzenesulfonyl chloride (BSC; 2.48 gmole) is charged. Addition of NaCN at a rate to complete the addition in 90 minutes is started. The temperature is held at <5° C. using brine. The reaction mass pH is controlled at 9.5-10 using 5% caustic. After the NaCN charge, the reactor is held at 5° C. and pH 10 for 30-45 minutes. A check for BSC via gas chromatography (6'×¼" glass column; 1% O.V. 101 or 3% O.V. 225) is made. When all of the BSC has reacted, the agitator is turned off. 300 g water is placed in a large separatory funnel and about half the reaction mass is added into the funnel.

The reaction mass is shaken to mix and to let the layers separate. The bottom product layer is bottled. The remainder of the reaction mass is run into the funnel, shaken and the layers are allowed to separate. The product layer is run into the same bottle. The water layer is treated with bleach and discarded. The combined product is weighted and submitted for analysis. Typically about 1450 g of solution assaying 32-33% is obtained for a yield of 93-95%.

Step C

Equipment as described in Step A above is used but no water trap is employed in the reflux system and a pH electrode and meter are used. To the addition funnel is charged 286 g 28.5% oximinophenylacetonitrile solution (0.485 gmole; 3% excess). To the reactor is charged 284 g 32.6% cyanomethylbenzenesulfonate in methylene chloride (0.471 gmole), 25 g water and 7.3 g 60% BTMAC (5 mole %). The reactor is heated to reflux at about 42° C. and addition of the oximinophenylacetonitrile is started. This addition is made in 15-20 minutes. After the addition, the reactor is held under reflux, maintaining a pH of 10.5 with slow 5% caustic addition as needed. The reaction mass is held 1.5 hours and then a check is made for unreacted cyanomethylbenzenesulfonate via gas chromatography (6' and ¼" glass column; 3% O.V. 225). When all of the cyanomethylbenzenesulfonate has reacted, the layers are allowed to separate and the bottom product layer is removed. The water layer is discarded.

Product Recovery and Purification: The methylene chloride is stripped on a rotary evaporator to maximum vacuum at 60° C. Methylene chloride is reduced to below 0.5%. The crude product typically weighs about 84 g. 4.8 g of 2-propanol per gram of crude product is charged and warmed to 50° C. to dissolve the product. The reaction mass is chilled to −10° C. to precipitate the product. The product is filtered on a Buchner funnel and is drawn for at least two hours to air dry the product cake. Typically about 70 g of recrystallized product is obtained, assaying 98.5-99% for an overall yield of 79-80% (reaction and purification).

The following compounds can be produced by the methods described above:

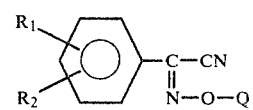

| | $R_1$ | $R_2$ | Q | °C. |
|---|---|---|---|---|
| Ex 3 | 4-Br | H | —$CH_2$—CN | m.p. 77°-79° |
| Ex 4 | H | H | —$CH_2$—$CH_2$—CN | m.p. 123°-126° |
| Ex 5 | H | H | —$CH_2$—$CH_2$—$CH_2$—CN | oil |

-continued

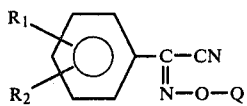

| | $R_1$ | $R_2$ | Q | °C. |
|---|---|---|---|---|
| Ex 6 | 2-$CH_3$ | H | —$CH_2$—CN | |
| Ex 7 | 2-F | H | —$CH_2$—CN | |
| Ex 8 | 4-n-$C_4H_7O$ | H | —$CH_2$—N | |
| Ex 9 | H | H | —$CH(CH_3)$—CN | m.p. 60°–62° |
| Ex 10 | 4-$CH_3$ | H | —$CH_2$—CN | m.p. 82°–84° |
| Ex 11 | 3-$CH_3$ | 4-$CH_3$— | —$CH_2$—CN | m.p. 40° |
| Ex 12 | H | 4-$CH_3O$— | —$CH_2$—CN | m.p. 91°–93° |
| Ex 13 | 4-Cl | H | —$CH_2$—CN | m.p. 69°–71° |
| Ex 14 | 2-Cl | H | —$CH_2$—CN | m.p. 51°–53° |
| Ex 15 | 2-Cl | 4-Cl | —$CH_2$—CN | m.p. 126°–128° |
| Ex 16 | 3-Cl | 4-Cl | —$CH_2$—CN | m.p. 90°–93° |

EXAMPLE 17

O-cyanomethyloximinonaphthylacetonitrile of melting point 81°–82° C. and analagous compounds may be prepared from the appropriate naphthylacetonitriles and aldehydes, ketones or benzophenones.

The following heterocyclic oxime compounds can be produced similarly:

| Example | $R_4$ | Z | Q | |
|---|---|---|---|---|
| 18 | H | S | $CH_2CN$ | oil |
| 19 | 5-Cl | S | $CH_2CN$ | |
| 20 | H | O | $CH_2CN$ | oil |
| 21 | 5-$NO_2$ | O | $CH_2CN$ | oil |
| 22 | 5-Cl | O | $CH_2CN$ | oil |

What is claimed is:

1. A process for the manufacture of compounds of the formula (I)

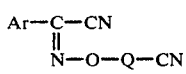

wherein Q represents lower alkylene or phenalkylene;
Ar represents a phenyl group of the formula:

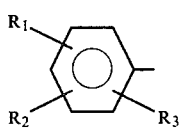

an α- or β-naphthyl group; or
a heterocyclic group of the formula:

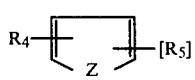

$R_1$ represents hydrogen, halogen, lower alkyl, lower alkoxy, or a phenoxy group which is in the para position and which is optionally substituted a maximum of twice by halogen, CN, $NO_2$, or $CF_3$;

$R_2$ and $R_3$ independently represent hydrogen, halogen, lower alkyl, $NO_2$, lower alkoxy, lower halogenoalkyl;

$R_4$ represents hydrogen, halogen, lower alkyl, lower akloxy, and $NO_2$;

Z represents oxygen or sulfur;

which comprises condensing a cyano sulfonate of the formula

Ph-$SO_3$-Q-CN wherein PH-$SO_3$-is an aromatic protecting group with Ph being phenyl or p-methyl substituted phenyl with an oximinoaryl nitrile having the formula:

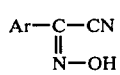

or the alkali metal salt thereof, at a temperature of about 25°–140° C., prepared by reacting an aryl sulfonyl halide of the formula Ph-$SO_2$-X wherein X is halogen with a carbonyl compound of the formula

O=Q and an alkali metal cyanide in the presence of a phase-transfer catalyst at a temperature of about 0°–°20° C. and said oximinoaryl nitrile having been prepared by the nitrosation of an aryl acetonitrile of the formula Ar-$CH_2$-CN with a lower alkyl nitrite ester in the presence of an alkali metal hydroxide at an initial temperature of 10°–50° C., and at a subsequent temperature of about 100°–110° C.

2. A process for the manufacture of compounds of the formula (I)

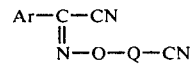

wherein Q represents lower alkylene or phenalkylene;
Ar represents a phenyl group of the formula:

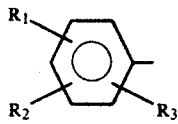

an α- or β-naphthyl group; or
a heterocyclic group of the formula:

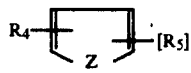

$R_1$ represents hydrogen, halogen, lower aklyl, lower alkoxy, or a phenoxy group which is in the para position and which is optionally substituted a maximum of twice by halogen, CN, $NO_2$, or $CF_3$;

$R_2$ and $R_3$ independently represent hydrogen, halogen, lower alkyl, $NO_2$, lower alkoxy, lower halogenoalkyl;

$R_4$ represents hydrogen, halogen, lower alkyl, lower alkoxy, and $NO_2$;

Z represents oxygen or sulfur;
which comprises condensing a cyano sulfonate of the formula Ph-SO$_3$-Q-CN wherein Ph-SO$_3$- is an aromatic protecting group with Ph being phenyl or p-methyl substituted phenyl with an oximinoaryl nitrile having the formula;

or the alkali metal salt thereof at a temperature of about 25°–140° C.

3. The process according to claim 1 wherein said oximinoaryl nitrile is prepared by the nitrosation of an aryl acetonitrile of the formula:

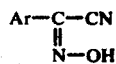

with a lower alkyl nitrite ester in the presence of about a one molar excess of an alkali metal hydroxide.

4. The process according to claim 3 wherein said nitrite ester is isopropyl nitrite.

5. The process according to claim 1 wherein said cyanosulfonate is prepared by reacting a sulfonyl chloride of the formula Ph-SO$_2$Cl in a water-immiscible solvent with an aqueous solution of excess alkali metal cyanide and a carbonyl compound of the formula O=Q in the presence of 1–5 mole % of a phase-transfer catalyst.

6. The process according to claim 1 wherein said condensation is accomplished by dissolving the cyanosulfonate and the oximinoaryl nitrile each in a mutually immiscible solvent and then mixing the resulting solutions with each other in the presence of 1–5 mole % of a phase-transfer catalyst.

7. The process according to claim 6 wherein said immiscible solvents are water and water-immiscible reactant-inert hydrocarbon or chlorinated hydrocarbon.

8. The process according to claim 5 or 6 wherein said phase-transfer catalyst is a quaternary ammonium salt.

9. The process according to claim 3, wherein said resulting oximinoaryl nitrile is formed as the cis- and trans-isomers and the nitrosation reaction medium is maintained at a temperature level at which thermal isomerization of the trans-isomer to the cis-isomer is substantially completed.

10. The process according to claim 9 wherein said compound of formula (I) is (cis-) O-cyanomethyloximinophenylacetonitrile, said arylacetonitrile is phenylacetonitrile and said carbonyl compound is formaldehyde.

11. The process according to claim 6 wherein said cyanosulfonate is formed by dissolving benzenesulfonyl chloride in methylene chloride, adding thereto formaldehyde and a quaternary ammonium salt as phase-transfer catalyst, and then, with agitation and cooling, adding rapidly an aqueous solution of sodium cyanide to initiate and complete said phase-transfer reaction within about 2 hours.

12. The process according to claim 5 or 6 wherein about 2.5 mole % of said phase-transfer catalyst is present.

* * * * *

UNITED STATES PATENT AND TRADEMARK OFFICE
CERTIFICATE OF CORRECTION

PATENT NO. : 4,260,555
DATED : APRIL 7, 1981
INVENTOR(S) : HAL L. MYATT

It is certified that error appears in the above—identified patent and that said Letters Patent is hereby corrected as shown below:

Claim 1, Column 12, Line 24 reads:

"akloxy, and NO$_2$;"  Should read:  "alkoxy, and NO$_2$;"

Claim 1, Column 12, Lines 40-41 read:

"25°-140°C., prepared by reacting an aryl sulfonyl halide of the formula"

Should read:

"25°-140°C., said cyanosulfonate having been prepared by reacting an aryl sulfonyl halide of the formula"

Signed and Sealed this

First Day of December 1981

[SEAL]

Attest:

GERALD J. MOSSINGHOFF

Attesting Officer    Commissioner of Patents and Trademarks